United States Patent [19]

Omodei-Sale et al.

[11] E Re. 30,456

[45] Reissued Dec. 23, 1980

[54] 2-SUBSTITUTED PHENYL-S-TRIAZOLO[5,1-a] ISOQUINOLINE COMPOUNDS

[75] Inventors: Amedeo Omodei-Sale, Voghera; Pietro Consonni; Leonard Lerner, both of Milan, all of Italy

[73] Assignee: Gruppo Lepetit S.p.A., Milan, Italy

[21] Appl. No.: 32,205

[22] Filed: Apr. 23, 1979

Related U.S. Patent Documents

Reissue of:

[64] Patent No.: 4,075,341
Issued: Feb. 21, 1978
Appl. No.: 636,330
Filed: Nov. 28, 1975

U.S. Applications:

[63] Continuation-in-part of Ser. No. 473,045, May 24, 1974, abandoned.

[30] Foreign Application Priority Data

May 25, 1973 [GB] United Kingdom ..... 25163/73
Aug. 22, 1973 [GB] United Kingdom ..... 39789/73

[51] Int. Cl.[3] ..... C01D 471/04; A61K 31/53
[52] U.S. Cl. ..... 424/258; 546/82
[58] Field of Search ..... 424/258; 546/82

[56] References Cited

U.S. PATENT DOCUMENTS

| | | | |
|---|---|---|---|
| 2,976,146 | 3/1961 | Salminen et al. | 424/258 |
| 3,652,570 | 3/1972 | Gittos et al. | 424/258 |
| 3,758,480 | 9/1973 | Reimlinger et al. | 424/258 |
| 3,775,417 | 11/1973 | de Ruiter et al. | 424/258 |

FOREIGN PATENT DOCUMENTS

| | | | |
|---|---|---|---|
| 780885 | 3/1972 | Belgium | 424/258 |
| 883836 | 10/1971 | Canada | 424/258 |
| 884328 | 10/1971 | Canada | 424/258 |

*Primary Examiner*—Mary C. Lee

[57] ABSTRACT

A new process for preparing s-triazolo[5,1-a]-isoquinoline derivatives of the formula

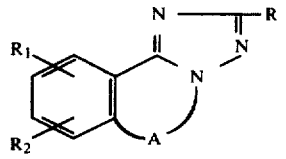

I wherein A represents the group —$CH_2$—$CH_2$— or —CH=CH—; R is selected from hydrogen, amino, lower alkylamino, di-lower alkylamino, acylamino, diacylamino, ureido, thioureido, carbethoxythioureido, benzoylthioureido, sulfhydryl, lower alkyl, trifluoromethyl, phenyl, substituted phenyl, pyridyl, methylpyridyl and dimethylpyridyl; and $R_1$ and $R_2$ each independently represents hydrogen or lower alkoxy, by condensation of a 2-amino-3,4-dihydro-1(2H)-isoquinolinone with an imidolyl, cyanamide, cyanic or thiocyanic derivative.

New compounds of the formula I wherein A represents the group —$CH_2$—$CH_2$— or —CH=CH—, R has the same meaning as above with the exclusion of hydrogen, methyl, phenyl, and trifluoromethyl, $R_1$ and $R_2$ have the same meaning as above, with the proviso that when A represents the group —CH=CH—, R cannot be tolyl or pyridyl.

The new compounds and some of the intermediates of the process are active as antiinflammatories, CNS depressants and anti-fertility agents.

14 Claims, No Drawings

2-SUBSTITUTED PHENYL-S-TRIAZOLO[5,1-a] ISOQUINOLINE COMPOUNDS

Matter enclosed in heavy brackets [ ] appears in the original patent but forms no part of this reissue specification; matter printed in italics indicates the additions made by reissue.

CROSS-REFERENCE TO RELATED APPLICATION

This application is a continuation-in-part of application Ser. No. 473,045 filed May 24, 1974 now abandoned.

SUMMARY OF THE INVENTION

This invention relates to a new process for preparing s-triazolo[5,1-a]isoquinoline derivatives of the formula

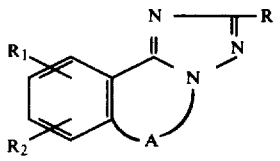

I wherein A represents the group —$CH_2$—$CH_2$— or —CH=CH—; R is selected from hydrogen, amino, lower alkylamino, di-lower alkylamino, acylamino, diacylamino, ureido, thioureido, carbethoxythioureido, benzoylthioureido, sulfhydryl, lower alkyl, trifluoromethyl, phenyl, substituted phenyl, pyridyl, methylpyridyl and dimethylpyridyl; and $R_1$ and $R_2$ each independently represents hydrogen or lower alkoxy.

In the specification and claims the term and the portion "acyl" identifies lower alkanoyl radicals derived from an aliphatic acid of 1 to 6 carbon atoms, e.g., formyl, acetyl, propionyl, butyryl, isobutyryl, pentanoyl, pivaloyl and hexanoyl.

The term "substituted phenyl" identifies phenyl radicals which carry one to three substituents independently selected from lower alkyl, lower alkoxy, lower alkenyloxy, lower alkynyloxy, methylenedioxy, halo, trifluoromethyl, hydroxy, cyclopropyloxy, cyclobutyloxy, cyclopentyloxy, cyclohexyloxy, benzyloxy, carboxymethoxy, carbo(lower alkoxy)methoxy, amino, lower akylamino, dilower alkylamino, acylamino and nitro.

The term "lower alkyl" and the portion "lower alkyl" in the term "lower alkylamino" identify a branched or linear aliphatic radical containing from 1 to 5 carbon atoms, such as methyl, ethyl, propyl, butyl, isobutyl, tert-butyl, pentyl and neopentyl.

The term "lower alkoxy" designates a branched or linear 1 to 5 carbon atom alkoxy group, e.g., methoxy, ethoxy, propoxy, isopropoxy, isobutoxy, tert-butoxy, pentyloxy, isoamyloxy, 2-methylbutoxy, and neopentyloxy.

The term "lower alkenyloxy" identifies a branched or linear 3 to 5 carbon atom alkenyloxy group, e.g., allyloxy, 2-butenyloxy, 1-methyl-2-propenyloxy, 1,1-dimethyl-2-propenyloxy, 3-methyl-2-butenyloxy, 2-pentenyloxy, 3-pentenyloxy and 4-pentenyloxy.

The term "lower alkynyloxy" identifies a branched or linear 3 to 5 carbon atom alkynyloxy group, e.g., propargyloxy, 2-butynyloxy, 1-methyl-2-propynyloxy, 1,1-dimethyl-2-propynyloxy, 3-methyl-2-butynyloxy, 2-pentynyloxy, 3-pentynyloxy and 4-pentynyloxy.

The term "halo" designates chloro, bromo or fluoro.

This invention also concerns the new compounds of the formula I wherein A represents the group —$CH_2$—$CH_2$— or —CH=CH—, R has the same meaning as above with the exclusion of hydrogen, lower alkyl, phenyl, tolyl and trifluoromethyl; $R_1$ and $R_2$ have the same meanings as above, with the proviso that when A represents the group —CH=CH—, R cannot be pyridyl.

The new compounds of this invention are useful as antiinflammatories, CNS depressants and anti-fertility agents. Some s-triazolo[5,1-a]isoquinoline compounds and processes for their manufacture which are not within the scope of this invention are described or mentioned in U.S. Pat. Nos. 3,758,480 and 3,775,417 and in Chem. Ber. 104: 3965-3975 (1971). The process described in the cited literature for the preparation of these latter compounds is, however, different from that described and claimed in this application. Moreover, the activity and the utility disclosed in U.S. Pat. Nos. 3,758,480 and 3,775,417 does not refer to the pharmaceutical or biological area as in our application since the compounds are therein described as hydrogen halide acceptors or corrosion inhibitors in cooling liquids. U.S. Pat. No. 3,652,570 discloses some s-triazolo[3,4-a]isoquinoline derivatives, i.e., compounds pertaining to a different ring system, wherein the nitrogen atom bridging s-triazole and isoquinoline is not directly bound to a second nitrogen atom of the triazole ring. Moreover, the substituents on the triazole moiety disclosed in the foregoing U.S. patent are only the following: oxy, lower alkyl, amino, lower acyl and guanidino.

A preferred group of compounds of this invention comprises those compounds of the formula 1 wherein the symbol R is a "substituted phenyl" radical of the formula

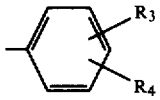

wherein one of the substituents $R_3$ and $R_4$ is located in the 3- or 4-position of the phenyl radical, and represents a lower alkoxy, lower alkenyloxy, lower alkynyloxy, halo, trifluoromethyl, hydroxy, cyclopropyloxy, cyclobutyloxy, cyclopentyloxy, benzyloxy, nitro or dimethylamino group and the other represents hydrogen, methoxy or halo, or $R_3$ and $R_4$ taken together represent a methylenedioxy group, the symbols $R_1$ and $R_2$ both represent hydrogen, and the symbol A represents the —$CH_2$—$CH_2$— or —CH=CH— group. The group of compounds defined above shows an interesting antifertility activity.

A most preferred group of compounds comprises those compounds of the group defined as hereinabove, where one of $R_3$ and $R_4$ is located in the 3- or 4-position of the phenyl ring and represents methoxy, ethoxy, propoxy, isopropoxy, allyloxy, propargyloxy or halo and the other represents hydrogen. This latter group of compounds shows a very remarkable antifertility activity.

This invention also concerns a method for preventing littering in impregnated female animals. According to this method, impregnated female animals are administered an effective amount of a compound of the formula I wherein the symbol R is a "substituted phenyl" radical of the formula

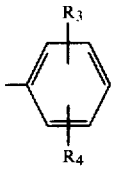

wherein one of the substituents $R_3$ and $R_4$ is located in the 3- or 4-position of the phenyl radical, and represents a group lower alkoxy, lower alkenyloxy, lower alkynyloxy, halo, trifluoromethyl, hydroxy, cyclopropyloxy, cyclobutyloxy, cyclopentyloxy, benzyloxy, nitro or dimethylamino and the other represents hydrogen, methoxy or halo, or $R_3$ and $R_4$ taken together represent a methylenedioxy group, the symbols $R_1$ and $R_2$ both represent hydrogen, and the symbol A represents the $-CH_2-CH_2-$ or $-CH=CH-$ group and salts thereof with a pharmaceutically acceptable acid.

The process of this invention is summarized by the following scheme:

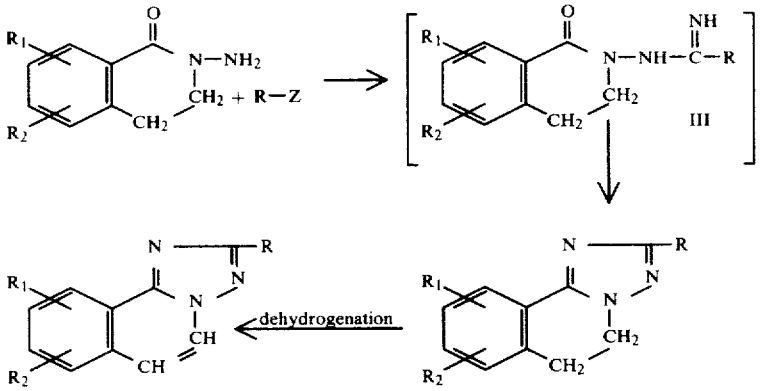

wherein R and $R_1$ have the same meanings as above, and Z represents one of the following groups:

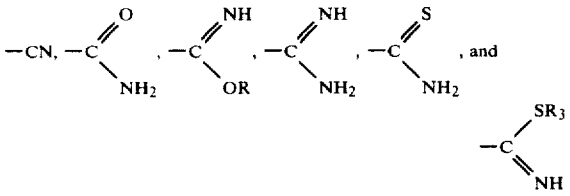

wherein $R_3$ is $C_1$-$C_4$ alkyl.

Both reactants may be used as free compounds or as their corresponding acid or basic salts. For example, the compound II may be utilized in the form of its hydrochloride while the compound R—Z, when representing a thiocyanic acid, i.e. HSCN, may be employed in the form of its salt with an alkali metal, or when R—Z is an imidoether, it may be used in the form of its hydrochloride.

In actual practice, the reaction is effected in two steps, but the isolation of intermediate III is not strictly necessary. However, in some cases it is preferred to isolate and characterize the open chain derivatives III, since some of these compounds show interesting properties as antiinflammatories, analgesics and CNS depressants. A particular group of compounds of formula III which exhibits remarkable pharmacological activities of this type comprises those derivatives where R is phenyl or substituted phenyl (defined as above). The first condensation step of the reaction process is carried out by treating for 3 to 30 hours at a temperature ranging from about 60° to about 160° C. the 2-amino-3,4-dihydroisoquinolinone II with a compound of formula R—Z. Although the proportions of the reactants is not strictly critical, in most cases, an excess of this latter reactant is employed to obtain higher yields. Moreover, a small amount of an acidic substance catalyzes the condensation reaction. Generally, the acidic catalyst consists of a hydrohalide which is introduced into the reaction mixture. When it is possible, the hydrohalide catalyst is employed as a hydrohalide salt of the reactant R—Z. As a practical example, the first step of the reaction is effected, e.g., by heating one molecular proportion of 2-amino-3,4-dihydroisoquinolinone II with about 1.5 molecular proportions of the ethyl ester of benzimidic acid and 0.1 molecular proportion of the hydrochloride of said ester.

The compound resulting from the condensation is 2-benzimidoylamino-3,4-dihydro-1 (2H)-isoquinolinone of the formula III.

To complete the reaction according to scheme 1, the obtained mixture containing the intermediate III is dissolved in a solvent such as a lower alkanol and, after addition of a basic catalyst, which, for instance, may consist of about 0.5 molecular proportions of a strong base, such as sodium hydride or an alkali metal lower alkoxide, it is refluxed for 3 to 8 hours.

The final product I is then recovered according to usual procedures, which comprise evaporation of the reaction solvent, dissolving the crude solid in a water immiscible organic solvent, washing with water, evaporating the organic phase and purifying the product by crystallization or column chromatography.

If it is desired to isolate the intermediate III, the mixture derived from the first reaction step is washed with aqueous sodium bicarbonate and water and the crude product is purified by crystallization from a suitable solvent.

The reactants of formula II which may be employed according to scheme 1 are prepared according to the procedure described in Belgian Pat. No. 780,885. As starting compounds R—Z, there are preferably employed imidates, cyanamide, cyanic and thiocyanic acid derivatives.

Dehydrogenation of the compounds obtained according to the procedure described above afford compounds wherein A represents the group —CH=CH— as reported in scheme 1.

Among the several useful dehydrogenating agents, which may be employed are sulfur, N-bromoacetamide, bromine, lead tetraacetate, mercuric acetate, chloranil, dichlorodicyanoquinone and manganese dioxide. This latter may be prepared in a wet state as described by E. Pratt and J. Van de Castle in J. Org. Chem., 26,2973, (1961) and is employed under conditions reported by J. Goldman et al., J. Org. Chem., 34; 1979, (1969).

Generally, the reaction is carried out in the presence of a solvent, which is preferably selected from inert organic liquids, such as, for instance, benzene, dioxane, tetrahydrofuran, carbon tetrachloride and the like. The dehydrogenating agent may be added in the same proportion as the triazoloisoquinoline compound, or in a considerably large molar excess if manganese dioxide is used, but this does not cause any disadvantage, because it is easily removed from the reaction mixture by simple filtration.

After the reaction is completed and the catalyst is eventually filtered off, the resulting solution is evaporated to dryness and a residue is obtained which may be successively purified according to known procedures, such as, for instance, by column chromatography, by distillation under reduced pressure if the residue is an oily distillable substance, or by recrystallization from a suitable solvent if it is a solid.

The yields of the inventive process are better than those of the prior art. For instance, the compound 2-phenyl-s-triazolo[5,1-a]isoquinoline is obtained according to the process herein with an overall yield of about 66 percent (from 2-amino-3,4-dihydroisoquinolinone), while the same compound is obtained only in a 35 percent overall yield (from 1-aminoisoquinoline) according to the process of Canadian Pat. No. 884,328.

The compound 2-methyl-5,6-dihydro-s-triazolo[5,1-a]isoquinoline is obtained according to our process (from 2-amino-3,4-dihydro-1(2H)-isoquinolinone) in an overall yield of about 85 percent while the yield according to the processes described in Canadian Pat. Nos. 884,328 and 883,836 is only about 25 percent (from 1-aminoisoquinoline).

Some compounds of formula I may also be obtained through chemical modification of other compounds falling within the same formula I prepared according to the reaction scheme outlined above. For instance, compounds of formula I wherein R is acylamino or diacylamino are prepared by acylation of the corresponding derivative wherein R is amino. Compounds of formula I wherein R is lower alkylamino are prepared by reduction of the corresponding acylamino or aldimino derivative with lithium aluminum hydride. Catalytic hydrogenation of a mixture of a compound of formula I wherein R is amino with excess of a lower aliphatic aldehyde affords compounds of formula II wherein R is di-lower alkylamino. Compounds wherein R is thioureido are prepared by hydrolytic cleavage (e.g., by boiling in dilute sodium hydroxide) of the corresponding carbethoxy and benzoyl-thioureido derivatives, which in turn are obtained from the 2-amino derivatives and carbethoxy- or benzoylisothiocyanate. Desulfurization of the thioureido derivative (e.g. with $H_2O_2$ and alkali) leads to the corresponding ureido derivative.

Compounds of formula I wherein R is hydrogen are prepared from the corresponding derivatives wherein R is amino by treatment with sodium nitrite in an acidic medium followed by reduction with $H_3PO_2$. The compound wherein R is hydroxyphenyl is prepared by hydrogenolysis of the corresponding benzyloxyphenyl derivative. Accordingly, the compounds wherein R is phenyl substituted with lower alkyloxy, lower alkenyloxy, lower alkynyloxy, cyclopropyloxy, cyclobutyloxy, cyclopentyloxy, cyclohexyloxy, are prepared by reaction of the hydroxyphenyl derivative with a suitable agent such as a lower alkyl, lower alkenyl, lower alkynyl, cyclopropyl, cyclobutyl, cyclopentyl and cyclohexyl halide and their corresponding tosylates and mesylates. Moreover, by reacting compounds of formula I wherein R is hydroxyphenyl with an α-haloacetic acid or its lower alkyl ester in the presence of an acid acceptor the corresponding compounds wherein R is carboxymethoxyphenyl and carbo(lower alkoxy)methoxyphenyl are obtained.

The compounds wherein R is aminophenyl, lower akylaminophenyl di-lower alkylaminophenyl and acylaminophenyl are, in turn, obtained from the corresponding nitro derivative through catalytic hydrogenation followed by a usual alkylation and acylation procedure.

The anti-inflammatory activity of some inventive compounds was evidenced by means of the carrageenin test in rats. Doses from about 20 to about 100 mg./kg. of representative compounds were proved to be effective in inhibiting the growth of the carrageenin induced edema. For instance, 2-ureido-5,6-dihydro-s-triazolo[5,1-a]isoquinoline and 2-sulfhydryl-5,6-dihydro-s-triazolo[5,1-a]isoquinoline show inhibition of about 35% of the edema when administered at 100 and 50 mg./kg. p.o., respectively.

The CNS depressant properties were investigated according to the Irwin method, and in particular, the anti-anxiety effect was evaluated on the basis of the secondary conditioned avoidance response test. A specific anti-anxiety effect was evidenced by administering to conditioned rats doses of 15–60 mg./kg. i.p. of representative compounds of the invention.

The following table indicates the ratio of the rats which were deconditioned after administration of a predetermined amount of a representative compound:

| Compound | Dose mg./kg. i.p. | Decondi-tioned/ treated | Toxicity $LD_{50}$ mg./kg. i.p. in mice |
|---|---|---|---|
| 2-Benzimidoylamino-3,4-dihydro-1 (2H)-isoquinolinone | 60 | 10/10 | >600 |
| 2-(m-Nitrobenzimidoylamino)-3,4-dihydro-1-(2H) isoquinoline | 60<br>30 | 10/10<br>6/10 | >600 |
| 2-Amino-5,6-dihydro-s-triazole-[5,1-a]isoquinoline | 30 | 6/10 | >600 |
| 2-(3-Pyridyl)-5,6-dihydro-s-triazolo[5,1-a]-isoquinoline | 15 | 10/10 | >400 |
| 2-acetamido-5,6-dihydro-s-triazole[5,1-a]isoquinoine | 60 | 7/10 | >400 |
| 2-diacetylamino-5,6-dihydro-s-triazole[5,1-a]isoquinoline | 60 | 6/9 | >600 |
| 2-carbethoxythioureido-5,6-dihydro-s-triazole- | | | |

-continued

| Compound | Dose mg./kg. i.p. | Decondi-tioned/ treated | Toxicity $LD_{50}$ mg./kg. i.p. in mice |
|---|---|---|---|
| [5,1-a]isoquinoline | 60 | 7/10 | >600 |

A particular group of compounds of this invention comprises those derivatives of formula I which are useful as anti-fertility agents. These compounds show this utility when administered to laboratory animals, e.g., rats, hamsters, dogs and monkeys. Moreover, the anti-fertility activity of these new compounds is not associated with other biological effects which are usual with hormonal substances.

Fertility regulation can usually be achieved in a number of ways through the administration of hormonal substances. These can involve ovulation inhibition, ova transport, fertilization, implantation of the zygote, resorption of the fetus or abortion. Only with ovulation inhibition has there developed a successful method that is clinically useful.

The compounds of this invention which pertain to the group identified above allow an entirely new approach to this problem in which a non-hormonal compound can be administered parenterally or orally on a once or more times per month basis or as needed for a "missed period" or to induce termination of a more advanced pregnancy.

Representative experiments for assessing anti-fertility activity are carried out with female Syrian golden hamsters weighing 100 to 130 g. The animals are mated and the presence of sperm in the vagina is taken as evidence of mating. The day sperm is detected is considered day one of pregnancy, since in our laboratories and those of other investigators 90 to 100% of animals that mate as evidenced by vaginal sperm are pregnant. Pregnancy is later confirmed at the time of autopsy by presence of fetuses or implantation sites in the uterus. Even if an animal aborts the fetus, implantation scars still remain as evidence that the animal had been pregnant. Test compounds dissolved or suspended in sesame oil are administered subcutaneously in doses of 10 mg./kg. daily for 5 days beginning on day 4 of pregnancy (days 4–8). The animals are autopsied on day 14 of pregnancy and the uteri are examined for evidence of pregnancy (implantation sites, fetal resorptions or live fetuses), hemorrage, and evidence of abnormalities of the uterus, placenta or fetuses. A compound is considered to be active if there is a reduction of live fetuses in at least 60% of the treated animals and the presence of implantation sites proves the animal to have been pregnant. In representative experiments the compounds of the following Examples prove to be active according to the above mentioned criteria: 1, 7, 8, 12, 13, 14, 15, 16, 19, 21, 22, 23, 24, 25, 27, 28, 31, 41, 42, 58 and 61. The compounds are then studied for dose-activity relationship and toxicity or other biological activities. Compounds that show 100% effectiveness (absence of live fetuses in 100% of animals) with minimal side effects or toxicity are studied in depth.

As an example, in following Table I are reported the $ED_{50}$ values of some representative novel 5,6-dihydro-s-triazole compounds in comparison with those of some related 5,6-dihydro compounds previously disclosed (U.S. Pat. Nos. 3,775,417 and 3,758,480) below the dashed line. The $ED_{50}$ values identify the dose levels which show 100% effectiveness (defined as above) in 50% of the treated animals.

TABLE I

| Compound 5,6-dihydro-5-triazolo [5,1-a]isoquinoline | $ED_{50}$ mg./kg.s.c. |
|---|---|
| 2-(m-Methoxyphenyl)- | 0.10 |
| 2-(m-Ethoxyphenyl)- | 0.03 |
| 2-(m-Propoxyphenyl)- | 0.11 |
| 2-(m-Chlorophenyl)- | 0.75 |
| 2-(p-Chlorophenyl)- | 0.065 |
| 2-(p-Fluorophenyl)- | 0.1 |
| 2-(m-Isopropoxyphenyl)- | 0.25 |
| 2-(m-Allyloxyphenyl)- | 0.18 |
| 2-(m-Propargyloxyphenyl)- | 0.21 |
| 2-Phenyl- | 1.0 |
| 2-(m-tolyl)- | >10 |
| 2-(o-tolyl)- | >10 |
| 2-(p-tolyl)- | 2.0 |
| 2-methyl- | >10 |

Table II reports data obtained in similar experiments employing 5,6-unsaturated compounds.

TABLE II

| Compound s-triazolo-[5,1-a]isoquinoline | $ED_{50}$ mg./kg. s.c. |
|---|---|
| 2-(m-Methoxyphenyl)- | 0.1 |
| 2-(4-Chlorophenyl)- | 0.08 |
| 2-Phenyl- | 0.25 |

The same criteria and conditions are also employed with rats with the exception that the animals (female Sprague-Dawley rats weighing 200–230g.) are treated on days 6 through 10 of pregnancy with a screening dose of 20 mg./kg. s.c. daily and are autopsied on day 16.

In performing experiments with dogs, female beagle dogs weighing approximately 10 kg. are mated and on the 20th day of pregnancy the animals are given single subcutaneous doses of the compounds that were active in both the rat and the hamster. On the 35th day of pregnancy, the animals are surgically opened and the uteri are examined for presence of fetuses, placental tissue etc. Following Table III reports the minimal doses of representative compounds showing a 100% effectiveness (absence of live fetuses in 100% of the animals).

TABLE III

| Compound 5,6-dihydro-s-triazolo [5,1-a]isoquinoline | Minimal effective doses mg./kg. s.c. |
|---|---|
| 2-(m-Methoxyphenyl)- | 12.5 |
| 2-(m-Ethoxyphenyl)- | 6.25 |
| 2-(m-Propoxyphenyl)- | 6.25 |
| 2-(m-Allyloxyphenyl)- | 6.25 |

The compounds of formula I and the intermediate of formula III have very low toxicities since generally their $LD_{50}$ values in mice are higher than 400 mg./kg.i.p. They are well tolerated at biologically active dosages. In particular, the compounds of Table III have $LD_{50}$ values in mice higher than 1500 mg./kg.i.p.

The compounds of the invention may be administered by various routes, for example, orally, subcutaneously, intravenously or intramuscularly. For oral administration, the substances are compounded in such forms as tablets, dispersible powders, capsules, granules, syrups, elixirs, and solutions. The compositions for oral use may contain one or more conventional adjuvants, such as, for instance, sweetening agents, flavoring agents, coloring agents, coating and preservative agents, in order to provide an elegant and palatable preparation. Tablets may contain the active ingredient admixed with conventional pharmaceutical acceptable excipients, e.g., inert diluents such as calcium carbonate, sodium carbonate, lactose and talc; granulating and disintegrating agents, such as, for instance, starch, alginic acid and sodium carboxymethylcellulose; binding agents, e.g., starch, gelatin, gum-arabic and polyvinylpyrrolidone; and lubricating agents, e.g., magnesium stearate, stearic acid and talc. The tablets may be uncoated or coated by known techniques to delay disintegration and absorption in the gastrointestinal tract in order to provide long-acting compositions. Syrups, elixirs and solutions are formulated as known in the art. Together with the active compound they may contain suspending agents, such as, for instance methylcellulose, hydroxyethylcellulose, tragacanth and sodium alginate; wetting agents, e.g., lecithin, polyoxyethylene stearates and polyoxyethylene sorbitan monooleate; and common preservative, sweetening and buffering agents. A capsule or a tablet may contain the active ingredient alone or admixed with an inert solid diluent, such as, for instance, calcium carbonate, calcium phosphate or kaolin.

Besides the oral route, other useful ways for administering the compounds of the invention may suitably be employed, such as, for instance, intravenously or intramuscularly. The active ingredient is thus embodied into injectable dosage forms. Such compositions are formulated according to the art and may contain appropriate dispersing or wetting agents and suspending or buffering agents identical or similar to those mentioned above. Sesame oil, benzyl alcohol, benzyl benzoate, peanut oil and their mixtures may suitably be employed as vehicles when the compounds are slightly soluble in aqueous media.

The compounds of the invention may also be administered in the form of their non-toxic pharmaceutically-acceptable acid addition salts. Such salts possess the same degree of activity as the free bases, from which they are readily prepared by reacting the base with an appropriate acid, and, accordingly, are included within the scope of the invention. Representative of such salts are the mineral acid salts, such as, for instance, the hydrochloride, hydrobromide, sulfate, phosphate and the like and the organic acid salts such as the succinate, benzoate, acetate, p-toluenesulfonate, benzene sulfonate, maleate, tartrate, methanesulfonate, cyclohexylsulfonate and the like.

The dosage of active ingredient employed for combatting inflammatory or anxious states in mammals, or for inhibiting reproduction, may vary depending on the compound employed and the severity of the condition being treated. Generally good results are obtained when compounds of the above formulas I and III are administered at a daily dosage of from about 0.8 to about 50 mg./kg. of animal body weight. The dosage forms useful for this purpose generally contain from about 10 to about 600 mg. of the active ingredient in admixture with a solid or liquid pharmaceutically-acceptable carrier or diluent.

DESCRIPTION OF SOME PREFERRED EMBODIMENTS

The following additional description and examples further describe the invention and the manner and process of making and using it to enable the art skilled to make and use the same and set forth the best mode contemplated by the inventors of carrying out the invention.

EXAMPLE 1

2-(m-Methoxyphenyl)-5,6-dihydro-s-triazolo[5,1-a]isoquinoline

A mixture of 16.2 g. of 2-amino-3,4-dihydro-1(2H)-isoquinolinone (0.10 mole), 27 g. of m-methoxybenzimidic acid ethyl ester (0.15 mole) and 2.15 g. of the hydrochloride of m-methoxybenzimidic acid ethyl ester is heated under vacuum (200 mm Hg.) for 5 hours at about 90° C. and for 2 hours at about 125° C. Then 3.50 g. of m-methoxybenzimidic acid ethyl ester (0.02 mole) is added and the mixture is heated for a further 16 hours at about 125° C. under vacuum. All volatile materials are eliminated by distilling off at 125° C. and 5 mm Hg. The solid residue may be used as such for the cyclization step or, after washing with aqueous sodium bicarbonate and water, may be purified by crystallization from ethanol to isolate the intermediate III, 2-(m-methoxybenzimidoylamino)-3,4-dihydro-1-(2H)-isoquinolinone (m.p. 176°-177° C.). The crude reaction product is cyclized by heating for five hours in 150 ml. of ethanol containing 1.2 g. of 80% sodium hydride (0.040 mole). The reaction mixture is then evaporated to dryness in vacuo and then dissolved in dichloromethane. The organic solution after washing with water is evaporated and the crude residual compound is crystallized from 50% ethanol, yielding 20 g. (72%) of the title compound, m.p. 94°-96° C.

The cyclization of the purified intermediate III may be effected according to the same procedure as given above.

EXAMPLES 2-31

By reacting 2-amino-3,4-dihydro-1(2H)-isoquinolinone with the imidic acid ethyl ester, A (following Table) in the presence of its hydrochloride essentially according to the procedure of Example 1, the 5,6-dihydro-s-triazolo[5,1-a]isoquinolines, B (following Table) are obtained.

The melting points (or boiling points) of the corresponding imidoylaminoisoquinolinone intermediates when isolated are also reported in the following Table.

TABLE I

| Example No. | A imidic acid ethyl ester | B 5,6-dihydro-s-triazolo[5,1-a]-isoquinoline | M.p., °C. or B.p., °C./mm Hg | Overall Yield, % | M.p. of the intermediates °C. |
|---|---|---|---|---|---|
| 2 | o-toluimidic | 2-(o-toluyl)- | 76-7 | 39 | |
| 3 | m-toluimidic | 2-(m-toluyl)- | 107-8 | 87 | 236-7 |
| 4 | p-toluimidic | 2-(p-toluyl)- | 125-7 | 81 | 203-4 |
| 5 | benzimidic | 2-phenyl- | 85-86 | 83 | 206-7 |
| 6 | o-chlorobenzimidic | 2-(o-chlorophenyl | 72-3 | 54 | |
| 7 | m-chlorobenzimidic | 2-(m-chlorophenyl) | 143-4 | 67 | 235-6 |

TABLE I-continued

| Example No. | A imidic acid ethyl ester | B 5,6-dihydro-s-triazolo[5,1-a]-isoquinoline | M.p., °C. or B.p., °C./mm Hg | Overall Yield, % | M.p. of the intermediates °C. |
|---|---|---|---|---|---|
| 8 | p-chlorobenzimidic | 2-(p-chlorophenyl)- | 174-5 | 79 | 228-30 |
| 9 | acetimidic | 2-methyl- | 63-5 | 85 | |
| 10 | nicotinimidic | 2-(3-pyridyl)- | 151-2 | 69 | |
| 11 | 3,4,5-trimethoxy-benzimidic | 2-(3,4,5-trimethoxyphenyl)- | 161-2 | 47 | |
| 12 | 3,5-dimethoxybenzimidic | 2-(3,5-dimethoxyphenyl)- | 124-6 | 49 | |
| 13 | m-ethoxybenzimidic | 2-(m-ethoxyphenyl)- | 102-3 | 80 | |
| 14 | m-propoxybenzimidic | 2-(m-propoxyphenyl)- | 116-7 | 80 | |
| 15 | m-benzyloxybenzimidic | 2-(m-benzyloxyphenyl)- | 112-3 | 79 | |
| 16 | 3,4-methylenedioxybenzimidic | 2-(3,4-methylenedioxyphenyl)- | 147-8 | 72 | 246-8 |
| 17 | isonicotinimidic | 2-(4-pyridyl)- | 158-9 | 60 | |
| 18 | m-trifluoromethylbenzimidic | 2-(m-trifluoromethylphenyl)- | 147-8 | 60 | 197-8 |
| 19 | m-fluorobenzimidic | 2-(m-fluorophenyl)- | 105-6 | 63 | 208-10 |
| 20 | 3,4-dimethylbenzimidic | 2-(3,4-dimethylphenyl)- | 143-4 | 56 | |
| 21 | m-isopropoxybenzimidic | 2-(m-isopropoxyphenyl)- | 106-7 | 68 | |
| 22 | m-pentyloxybenzimidic | 2-(m-pentyloxyphenyl)- | 71-3 | 72 | |
| 23 | m-cyclopentyloxybenzimidic | 2-(m-cyclopentyloxyphenyl)- | 76-8 | 54 | |
| 24 | m-allyloxybenzimidic | 2-(m-allyloxyphenyl)- | 96-7 | 78 | |
| 25 | m-propargyloxybenzimidic | 2-(m-propargyloxyphenyl)- | 113-4 | 71 | |
| 26 | m-nitrobenzimidic | 2-(m-nitrophenyl)- | 197-8 | 89 | 221-2 |
| 27 | p-dimethylaminobenzimidic | 2-(p-dimethylaminophenyl)- | 174-5 | 44 | |
| 28 | p-fluorobenzimidic | 2-(p-fluorophenyl)- | 121-2 | 72 | |
| 29 | propionimidic acid | 2-ethyl | 63-5 | 81 | |
| 30 | valerimidic acid | 2-n-butyl- | 135/0.05 | 75 | |
| 31 | m-butoxybenzimidic | 2-(m-butoxyphenyl)- | 61-3 | 80 | |

EXAMPLE 32

2-Amino-s-triazolo[5,1-a]isoquinoline

A mixture of 28 g. of 2-amino-3,4-dihydro-1(2H)-isoquinolinone hydrochloride (0.142 mole) and 6.26 g. of cyanamide (0.149 mole) in 270 ml. of anhydrous acetonitrile are refluxed for 2 hours and, after cooling, the precipitated solid is recovered by filtration. A sample of this product, i.e. the hydrochloride of 2-guanidino-3,4-dihydro-1(2H)-isoquinolinone recrystallized from ethanol melts at 261° C. (with decomposition).

This latter compound is added to a solution of 17.4 g. of 97% sodium hydroxide in 700 ml. of 80% ethanol and the mixture is refluxed for seven hours. The solvent is distilled off in vacuo and the solid residue is taken up with water and the pH of the mixture is brought to 7 by addition of acetic acid. The precipitated solid is filtered to give 24.4 g. (89%) of the title product, m.p. 164°-5° C. (from ethanol).

EXAMPLE 33

5,6-Dihydro-s-triazolo[5,1-a]isoquinoline

A mixture of 3.24 g. of 2-amino-3,4-dihydro-1(2H)-isoquinolinone (0.02 mole), 3.2 ml. of formamide (0.08 mole) and 0.02 g. of piperidine acetate is heated for 15 hours at 140° C. and the volatile materials are distilled off in vacuo. The residue is dissolved in 10 ml. of ethanol and 0.1 g. of 80% NaH is added to the solution which is then refluxed for 5 hours. The solvent is evaporated to dryness and the solid residue is extracted with several portions of boiling hexane. The obtained organic solution (25ml.) is kept for two days in a refrigerator and the solid precipitated is recovered by filtration. Yield 1 g. (30%), m.p. 84°-5° C. The same compound may be obtained in a 62% yield from 2-amino-5,6-dihydro-s-triazolo[5,1-a]isoquinoline by reaction with $NaNO_2$ in 2% sulfuric acid followed by addition of 50% aqueous $H_3PO_2$ at 40° C.

EXAMPLE 34

2-Diacetylamino-5,6-dihydro-s-triazolo[5,1-a]isoquinoline

2-Amino-5,6-dihydro-s-triazolo[5,1-a]isoquinoline (0.93 g.) is boiled for 4 hours in acetic anhydride (10 ml.) after distillation of the excess of the anhydride the residue is crystallized from ethanol. Yield g. 1.15 (85%). M.p. 139°-40° C.

EXAMPLE 35

2-Acetamido-5,6-dihydro-s-triazolo[5,1-a]isoquinoline

2-Amino-5,6-dihydro-s-triazolo[5,1-a]isoquinoline (0.93 g.) and acetic anhydride (0.565 ml.) are boiled for one hour in 10 ml. of benzene. After cooling, the solid precipitated is recovered on the filter and then is crystallized from ethyl acetate. Yield 0.95 g. (83%), m.p. 204°-6° C. The same compound may be obtained through partial hydrolysis with 5% HCl from the compound of Example 34.

EXAMPLE 36

2-Ethylamino-5,6-dihydro-s-triazolo[5,1-a]isoquinoline

2-Acetamido-5,6-dihydro-s-triazolo[5,1-a]isoquinoline is reduced with lithium aluminum hydride at 0°-10° C. in dimethoxyethane. Yield 53%, m.p. 100°-101° C.

EXAMPLE 37

2-Thioureido-5,6-dihydro-s-triazolo[5,1-a]isoquinoline

To a solution of 0.93 g. of 2-amino-5,6-dihydro-1(2H)-s-triazolo[5,1-a]isoquinoline (0.005 mole) in 20 ml. of acetonitrile, a solution of 0.66 g. of carbethoxyisothiocyanate (0.005 mole) in 4 ml. of acetonitrile is added at about 50° C. The mixture is then allowed to stand at room temperature for about five hours and then is cooled to about 5° C. The solid precipitated is recovered on the filter, yielding 1.4 g. of 2-carbethoxy-thioureido-5,6-dihydro-s-triazolo[5,1-a]isoquinoline, m.p. 195°-6° C. from ethanol.

An amount of 0.9 g. of the 2-carbethoxythioureido-5,6-dihydro-s-triazolo[5,1-a]isoquinoline is heated at 90° C. for half an hour in 25 ml. of 5% NaOH. The mixture is chilled and neutralized with dilute HCl. The crude 2-thioureido-5,6-dihydro-s-triazolo[5,1-a]isoquinoline is filtered and crystallized from 70% ethanol. Yield 0.65 g. (94%), m.p. 267°-8° C.

EXAMPLE 38

2-Sulfhydryl-5,6-dihydro-s-triazolo[5,1-a]isoquinoline

To 1.98 g. of 2-amino-3,4-dihydro-1(2H)-isoquinolinone hydrochloride (0.01 mole), 0.97 g. of potassium thiocyanate (0.01 mole) in 5 ml. of water is added at room temperature and, after 5 minutes, the mixture is cooled to 0° C. The solid precipitated is washed with cold water, then is gradually heated to about 140° C. in an open vessel. After 20 minutes at 140° C., the reaction mixture is cooled and the solid residue is crystallized from 60% ethanol giving 1.7 g. (81%) of 2-thioureido-3,4-dihydro-1(2H)-isoquinolinone, m.p. 225° C.

An amount of 0.66 g. of the 2-thioureido-3,4-dihydro-1(2H)-isoquinolinone (0.003 mole) is refluxed for 18 hours with 0.099 g. of 80% sodium hydride (0.0033 mole) in 10 ml. of isopropanol. Evaporation of the solvent gives a solid which is taken up with water and the solution is acidified to pH 5 with acetic acid. The solid precipitated is recovered on the filter and recrystallized from 80% ethanol. Yield 0.45 (74%), m.p. 236°-8° C.

EXAMPLE 39

2-(m-Aminophenyl)-5,6-dihydro-s-triazolo[5,1-a]isoquinoline 2-(m-Nitrophenyl)-5,6-dihydro-s-triazolo[5,1-a]isoquinoline (11.7 g.) is hydrogenated at atmospheric pressure and at room temperature in the presence of 3 g. of 10% Pd on charcoal. The product obtained is purified by crystallization from a 50:50 mixture of ethyl acetate and isopropyl ether. Yield 8.5 g. of the title product which melts at 118°-9° C.

EXAMPLE 40

2-(m-Acetamidophenyl)-5,6-dihydro-s-triazolo[5,1-a]isoquinoline

The title compound is obtained by refluxing for 3 hours 7.5 g. of 2-(m-aminophenyl)-5,6-dihydro-s-triazolo[5,1-a]isoquinoline with 3.28 ml. of acetic anhydride in 150 ml. of benzene. After evaporation of the solvent, the product is crystallized from ethanol; yield 7.4 g.; m.p. 225°-6° C.

EXAMPLE 41

2-(m-Dimethylaminophenyl)-5,6-dihydro-s-triazolo[5,1-a]isoquinoline 2-(m-Aminophenyl)-5,6-dihydro-s-triazolo[5,1-a]isoquinoline (1.31 g.) is stirred for 6 hours at room temperature with 1.42 ml. of dimethylsulfate in 8 ml. of benzene in the presence of 1.68 g. of sodium bicarbonate dissolved in 10 ml. of water. Extraction with dichloromethane and evaporation of the organic phase gives a crude product which, after purification by column chromatography through a silica gel column (eluent: benzene containing 2% of acetone), affords 1 g. of the title product, which melts at 192°-3° C.

EXAMPLE 42

2-(3-Hydroxyphenyl)-5,6-dihydro-s-triazolo[5,1-a]isoquinoline 2-(3-Benzyloxyphenyl)-5,6-dihydro-s-triazolo-[5,1-a]isoquinoline (17.7 g.) is dissolved in 500 ml. of ethanol and hydrogenated at atmospheric pressure and room temperature in the presence of 3 g. of 10% Pd on charcoal. After filtration of the catalyst, the solution is concentrated to 100 ml. The product which precipitates on cooling is purified by crystallization from ethanol. Yield 10.1 g.; m.p. 201°-2° C.

EXAMPLE 43

2-(3-Ethoxyphenyl)-5,6-dihydro-s-triazolo[5,1-a]isoquinoline 2-(3-Hydroxyphenyl)-5,6-dihydro-s-triazolo-[5,1-a]isoquinoline (3.95 g.) is added to 60 ml. of ethanol containing one equivalent proportion of sodium ethoxide. To this mixture is added 1.57 ml. of ethyl iodide in 15 ml. of ethanol. After stirring for one hour at room temperature, a further 1.57 ml. of ethyl iodide is added and the mixture is refluxed for 18 hours. The solvent is distilled off and the residue is washed with water and extracted with dichloromethane. Evaporation of the solvent and crystallization of the residue from ethanol gives 3.87 g. of the title product; m.p. 102°-3° C.

EXAMPLES 44-53

By alkylating 2-(3-hydroxyphenyl)-5,6-dihydro-s-triazolo[5,1-a]isoquinoline with reagents A according to the procedure described in Example 42 the compounds B are obtained.

| Example | A | B 5,6-dihydro-s-triazolo[5,1-a] isoquinoline | M.p. °C. |
|---|---|---|---|
| 44 | methyl iodide | 2-(m-methoxy-phenyl)- | 94-6 |
| 45 | isopropyl iodide | 2-(m-isopropoxy-phenyl)- | 106-7 |
| 46 | propyl bromide | 2-(m-propoxy-phenyl)- | 116-7 |
| 47 | butyl bromide | 2-(m-butoxy-phenyl)- | 61-3 |
| 48 | pentyl bromide | 2-(m-pentyloxy-phenyl)- | 71-3 |
| 49 | cyclopentyl bromide | 2-(m-cyclopentyl-oxyphenyl)- | 76-8 |
| 50 | allyl bromide | 2-(m-allyloxy-phenyl)- | 96-7 |
| 51 | propargyl | 2-(m-propargyl- | 113-4 |

-continued

| Example | A | B 5,6-dihydro-s-triazolo[5,1-a] isoquinoline | M.p. °C. |
|---|---|---|---|
| | bromide | oxyphenyl)- | |
| 52 | chloroacetic acid | 2-(m-carboxy-methoxyphenyl)- | 225-7 |
| 53 | ethyl chloro-acetate | 2-(m-carbethoxy-methoxyphenyl)- | 114-6 |

EXAMPLE 54

2-Ureido-5,6-dihydro-s-triazolo[5,1-a]isoquinoline

2-Thiureido-5,6-dihydro-s-triazolo[5,1-a]isoquinoline (1.2 g.) is suspended in 20 ml. of 2% aqueous sodium hydroxide and 1.9 ml. of 30% $H_2O_2$ is added at 40°-45° C. After 15 minutes, the mixture is heated for 5 minutes at 80° C. and, after cooling and neutralizing with dilute hydrochloric acid, the solid precipitate is recovered by filtration and purified by crystallization from 70% ethanol. Yield 0.8 g.; m.p. 210°-2° C.

EXAMPLE 55

2-Dimethylamino-5,6-dihydro-s-triazolo[5,1-a]isoquinoline

2-Amino-5,6-dihydro-s-triazolo[5,1-a]isoquinoline (4.65 g.) is dissolved in 100 ml. of ethanol and, after addition of 8 ml. of 40% formaldehyde and 30 ml. of acetic acid, the mixture is hydrogenated at room temperature and at a pressure of 5 atmospheres in the presence of one gram of 10% Pd on charcoal. After filtration of the catalyst, the solvent is evaporated off and the solid residue is crystallized from a 50:50 mixture of hexane and isopropyl ether. Yield 2.85 g.; m.p. 66°-8° C.

EXAMPLE 56

8,9-Dimethoxy-2-(m-methoxyphenyl)-5,6-dihydro-s-triazolo[5,1-a]isoquinoline

The title compound is prepared according to the procedure of Example 1 from 2-amino-5,6-dimethoxy-3,4-dihydro-1(2H)-isoquinolinone (prepared according to the procedure described in Belgian Pat. No. 780,885; m.p. 164°-6° C.) and m-methoxybenzimidic acid ethyl ester; m.p. 132°-3° C.

EXAMPLE 57

8-Methoxy-2-(m-methoxyphenyl)-5,6-dihydro-s-triazolo-[5,1-a]isoquinoline

The compound is prepared according to the procedure of Example 1 from 2-amino-6-methoxy-3,4-dihydro-1(2H)-isoquinolinone (prepared according to the procedure described in Belgian Pat. No. 780,885; m.p. 101°-3° C.) and m-methoxybenzimidic acid ethyl ester; m.p. 132°-3° C.

EXAMPLE 58

2-(m-Methoxyphenyl)-s-triazolo[5,1-a]isoquinoline

Thirty five grams of wet manganese dioxide, prepared as described by E. Pratt and J. Van de Castle, J. Org. Chem. 26, 2973 (1961) is suspended in 200 ml. of benzene, according to the procedure outlined by J. Goldman, J. Org. Chem. 34, 1979 (1969). The mixture is refluxed for about three hours, then a solution of 2.77 g. (0.010 mole) of 2-(m-methoxyphenyl)-5,6-dihydro-s-triazolo[5,1-a]isoquinoline in 30 ml. of anhydrous benzene is added. Refluxing is prolonged for a further six hours, then the reaction mixture is allowed to stand overnight. 20 Grams of the above manganese dioxide is added and the resulting suspension is refluxed for 8 hours. After cooling, the solid catalyst is filtered off, the benzene solution is dried under vacuum and a residue is obtained which is recrystallized from ethyl acetate. Yield 1.4 g., m.p. 159°-60° C. Alternatively, the title compound may be obtained in a 70% yield by treating at 200°-250° C. with about 1.5 equimolecular proportion of sulfur.

EXAMPLE 59

2-Phenyl-s-triazolo[5,1-a]isoquinoline

Following substantially the same procedures of Example 58, and starting from 2-phenyl-5,6-dihydro-s-triazolo[5,1-a]isoquinoline, the title compound is prepared. Yield 56%, m.p. 157°-8° C. (from ethyl acetate).

EXAMPLE 60

2-Phenyl-s-triazolo[5,1-a]isoquinoline

A mixture of 0.5 g. (0.002 mole) of 2-phenyl-5,6-dihydro-s-triazolo[5,1-a]isoquinoline and 0.28 g. (0.002 mole) of N-bromoacetamide in 10 ml. of carbon tetrachloride is refluxed for 5 hours. The crystalline precipitate which forms is filtered and dissolved in methylene chloride. The resulting solution is washed with sodium bicarbonate, then the solvent is evaporated off and the obtained residue recrystallized from ethyl acetate. Yield 79%.

EXAMPLE 61

2-(p-Chlorophenyl)-s-triazolo[5,1-a]isoquinoline

The compound is prepared according to the procedure of Example 60 by utilizing the compound of Example 8 as the starting material. M.p. 238°-240° C. The dehydrogenation may also be carried out with sulphur.

By operating according to the procedures of the foregoing examples, the following compounds are prepared:

2-(p-Methoxyphenyl)-5,6-dihydro-s-triazolo[5,1-a]isoquinoline
2-(o-Methoxyphenyl)-5,6-dihydro-s-triazolo[5,1-a]isoquinoline
2-(m-Cyclopropoxyphenyl)-5,6-dihydro-s-triazolo[5,1-a]isoquinoline
2-(m-Cyclobutoxyphenyl)-5,6-dihydro-s-triazolo[5,1-a]isoquinoline
2-(m-Isobutyrylaminophenyl)-5,6-dihydro-s-triazolo[5,1-a]isoquinoline
2-(p-Nitrophenyl)-5,6-dihydro-s-triazolo[5,1-a]isoquinoline
2-(p-Bromophenyl)-5,6-dihydro-s-triazolo[5,1-a]isoquinoline
2-(p-Trifluoromethylphenyl)-5,6-dihydro-s-triazolo[5,1-a]isoquinoline
2-(3,4-Dichlorophenyl)-5,6-dihydro-s-triazolo[5,1-a]isoquinolin
2-(m-Isobutoxyphenyl)-5,6-dihydro-s-triazolo[5,1-a]iso
2-[m-(tert-Butoxy)phenyl]-5,6-dihydro-s-triazolo[5,1-a]isoquinoline
2-[m-Isoamyloxyphenyl]-5,6-dihydro-s-triazolo[5,1-a]isoquinoline
2-(m-Cyclohexyloxyphenyl)-5,6-dihydro-s-triazolo[5,1-a]isoquinoline
2-Diethylamino-5,6-dihydro-s-triazolo[5,1-a]isoquinoline 2-Propylamino-5,6-dihydro-s-triazolo[5,1-a]isoquinoline
2-Butylamino-5,6-dihydro-s-triazolo[5,1-a]isoquinoline
2-Dibutylamino-5,6-dihydro-s-triazolo[5,1-a]isoquinoline
2-Benzoylthioureido-5,6-dihydro-s-triazolo[5,1-a]isoquinoline
2-(2-Pyridyl)-5,6-dihydro-s-triazolo[5,1-a]isoquinoline
2-(2,6-Dimethyl-4-pyridyl)-5,6-dihydro-s-triazolo[5,1-a]isoquinoline
2-(2-Methyl-4-pyridyl)-5,6-dihydro-s-triazolo[5,1-a]isoquinoline
2-(m-Ethylphenyl)-5,6-dihydro-s-triazolo[5,1-a]isoquinoline
2-(m-Isobutylphenyl)-5,6-dihydro-s-triazolo[5,1-a]isoquinoline
2-(m-Fluorophenyl)-s-triazolo[5,1-a]isoquinoline
2-(m-Hydroxyphenyl)-s-triazolo[5,1-a]isoquinoline
2-(m-Benzyloxyphenyl)-s-triazolo[5,1-a]isoquinoline
2-(m-Ethoxyphenyl)-s-triazolo[5,1-a]isoquinoline
2-(m-Allyloxyphenyl)-s-triazolo[5,1-a]isoquinoline
2-(m-Propargyloxyphenyl)-s-triazolo[5,1-a]isoquinoline
2-(m-Carbethoxymethoxyphenyl)-s-triazolo[5,1-a]isoquinoline
2-(3,4-Methylenedioxyphenyl)-s-triazolo[5,1-a]isoquinoline
2-(m-Propoxyphenyl)-s-triazolo[5,1-a]isoquinoline
2-(m-Cyclopropoxyphenyl)-s-triazolo[5,1-a]isoquinoline
2-(m-Isopropoxyphenyl)-s-triazolo[5,1-a]isoquinoline
2-(p-bromophenyl)-s-triazolo[5,1-a]isoquinoline
2-(p-Trifluoromethylphenyl)-s-triazolo[5,1-a]isoquinoline
2-(p-Nitrophenyl)-s-triazolo[5,1-a]isoquinoline
2-(3,4-dichlorophenyl)-s-triazolo[5,1-a]isoquinoline
2-(m-Cyclobutoxyphenyl)-s-triazolo[5,1-a]isoquinoline
2-(m-Cyclopentyloxyphenyl)-s-triazolo[5,1-a]isoquinoline
2-(m-Butoxyphenyl)-s-triazolo[5,1-a]isoquinoline
2-[m-(tert-Butoxyphenyl)]-s-triazolo[5,1-a]isoquinoline
2-(m-Pentyloxyphenyl)-s-triazolo[5,1-a]isoquinoline
2-(m-Cyclohexyloxyphenyl)-s-triazolo[5,1-a]isoquinoline
2-(m-Isoamyloxyphenyl)-s-triazolo[5,1-a]isoquinoline
2-(2,6-Dimethyl-4-pyridyl)-s-triazolo[5,1-a]isoquinoline
2-(m-Ethylphenyl)-s-triazolo[5,1-a]isoquinoline

EXAMPLE 62

A vial for injectable use is prepared containing compounded 2-(m-Methoxyphenyl)-s-triazolo[5,1-a]-

| | |
|---|---|
| isoquinoline | 30 mg. |
| Benzyl benzoate | 300 mg. |
| Sesame oil q.s. to | 2 ml. |

EXAMPLE 63

A vial for injectable use is prepared containing compounded 2-(m-Methoxyphenyl)-5,6-dihydro-s-triazolo[5,1-a]-

| | |
|---|---|
| isoquinoline | 35 mg. |
| Benzyl alcohol | 100 mg. |
| Peanut oil q.s. to | 2 ml. |

EXAMPLE 64

A vial for injectable use is prepared containing compounded 2-(m-Ethoxyphenyl)-5,6-dihydro-s-triazolo[5,1-a]-

| | |
|---|---|
| isoquinoline | 35 mg. |
| Benzyl alcohol | 100 mg. |
| Castor oil q.s. to | 2 ml. |

EXAMPLE 65

A capsule is prepared containing compounded 2-Pyridyl-5,6-dihydro-s-triazolo[5,1-a]-

| | |
|---|---|
| isoquinoline | 50 mg. |
| Talc | 5 mg. |
| Sodium carboxymethylcellulose | 5 mg. |
| Starch q.s. to | 150 mg. |

EXAMPLE 66

100 ml. Of a solution for oral use is prepared containing 2-(m-Chlorophenyl)-5,6-dihydro-s-triazolo[5,1-a]-

| | |
|---|---|
| isoquinoline | 800 mg. |
| Hydroxyethylcellulose | 0.5 mg. |
| Saccharine | 17 mg. |
| Water q.s. to | 100 ml. |

What is claimed is:

1. A compound of the formula

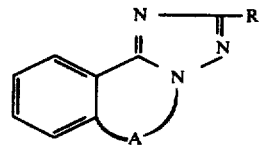

wherein A represents the group —$CH_2$—$CH_2$— or —CH=CH—; and wherein R is substituted phenyl of the formula

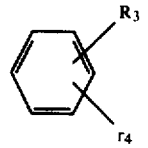

wherein one of the substituents $R_3$ and $R_4$ is located in the 3- or 4-position of the phenyl ring, and represents a lower alkoxy, lower alkenyloxy, lower alkynyloxy, fluoro, chloro, bromo, trifluoromethyl, hydroxy, cyclopropyloxy, cyclobutyloxy, cyclopentyloxy, benzyloxy, nitro or dimethylamino group and the other represents hydrogen, methoxy, fluoro, chloro or bromo; or $R_3$ and $R_4$ taken together represent a methylenedioxy group.

2. A compound as claimed in claim 1 wherein R is substituted phenyl of the formula

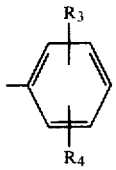

wherein one of $R_3$ and $R_4$ is located in the 3- or 4-position of the phenyl ring and represents methoxy, ethoxy, propoxy, isopropoxy, allyloxy, propargyloxy, fluoro, chloro or bromo and the other represents hydrogen.

3. The compound of claim 1 which is 2-(m-methoxyphenyl)-s-triazolo[5,1-a]isoquinoline.

4. The compound of claim 1 which is 2-(m-methoxyphenyl)-5,6-dihydro-s-triazolo[5,1-a]isoquinoline.

5. The compound of claim 1 which is 2-(m-ethoxyphenyl)-5,6-dihydro-s-triazolo[5,1-a]isoquinoline.

6. The compound of claim 1 which is 2-(m-propoxyphenyl)-5,6-dihydro-s-triazolo[5,1-a]isoquinoline.

7. The compound of claim 1 which is 2-(p-chlorophenyl)-5,6-dihydro-s-triazolo[5,1-a]isoquinoline.

8. The compound of claim 1 which is 2-(m-allyloxyphenyl)-5,6-dihydro-s-triazolo[5,1-a]isoquinoline.

9. The compound of claim 1 which is 2-(m-propargyloxyphenyl)-5,6-dihydro-s-triazolo[5,1-a]isoquinoline.

10. The compound of claim 1 which is 2-(m-chlorophenyl)-5,6-dihydro-s-triazolo[5,1-a]isoquinoline.

11. The compound of claim 1 which is 2-(m-isopropoxyphenyl)-5,6-dihydro-s-triazolo[5,1-a]isoquinoline.

12. The compound of claim 1 which is 2-(p-fluorophenyl)-5,6-dihydro-s-triazolo[5,1-a]isoquinoline.

13. A method for preventing littering in an impregnated female animal which comprises administering to said animal an effective amount of a compound of the following formula

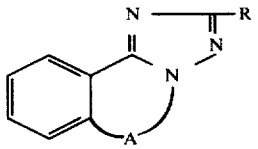

wherein R is substituted phenyl of the formula

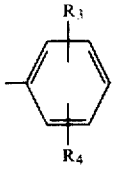

wherein one of the substituents $R_3$ and $R_4$ is located in the 3- or 4-position of the phenyl ring, and represents a lower alkoxy, lower alkenyloxy, lower alkynyloxy, fluoro, chloro, bromo, trifluoromethyl, hydroxy, cyclopropyloxy, cyclobutyloxy, cyclopentyloxy, benzyloxy, nitro or dimethylamino group and the other represents hydrogen, methoxy, fluoro, chloro or bromo; or $R_3$ and $R_4$ taken together represent a methylenedioxy group; and the symbol A represents the group $—CH_2—CH_2—$ or $—CH=CH—$.

14. A pharmaceutical composition for preventing littering in impregnated female animals comprising a pharmaceutical carrier and as the active ingredient an effective amount of a compound of the following formula

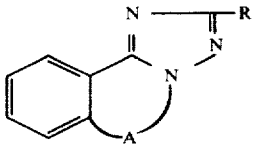

wherein R is substituted phenyl of the formula

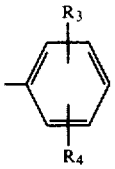

wherein one of the substituents $R_3$ and $R_4$ is located in the 3- or 4-position of the phenyl ring, and represents a lower alkoxy, lower alkenyloxy, lower alkynyloxy, fluoro, chloro, bromo, trifluoromethyl, hydroxy, cyclopropyloxy, cyclobutyloxy, cyclopentyloxy, benzyloxy, nitro or dimethylamino group and the other represents hydrogen methoxy, fluoro, chloro or bromo; or $R_3$ and $R_4$ taken together represent a methylenedioxy group; and the symbol A represents the group $—CH_2—CH_2—$ or $—CH=CH—$.

* * * * *

UNITED STATES PATENT AND TRADEMARK OFFICE

CERTIFICATE OF CORRECTION

PATENT NO. : Re. 30,456

DATED : December 23, 1980

INVENTOR(S) : Amedeo Omodei-Sale, et al.

It is certified that error appears in the above-identified patent and that said Letters Patent are hereby corrected as shown below:

Column 6, line 52, table, under Compound, "(2H)-isoquinoline" should read --(2H)isoquinolinone--.

Column 6, line 63, table, under Compound, "2-acctamido-5,6-dihydro-" should read --2-acetamido-5,6-dihydro--.

Column 6, line 64, table, under Compound, "noine" should read --noline--.

Column 8, line 5, Table 1, first column should read --Compound 5,6-dihydro-s-triazolo [5,1-a]isoquinoline--.

Column 16, line 60, should read --2-(m-Isobutoxyphenyl)-5,6-dihydro-s-triazolo[5,1-a]isoquinoline--.

Column 18, Claim 1, second formula should read

--

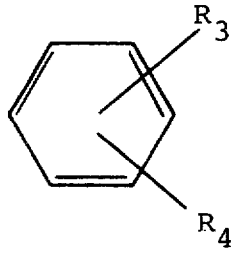

--.

UNITED STATES PATENT AND TRADEMARK OFFICE

CERTIFICATE OF CORRECTION

PATENT NO. : Re. 30,456

DATED : December 23, 1980

INVENTOR(S) : Amedeo Omodei-Sale, et al.

It is certified that error appears in the above-identified patent and that said Letters Patent are hereby corrected as shown below:

Column 19, Claim 13, formula should read

--

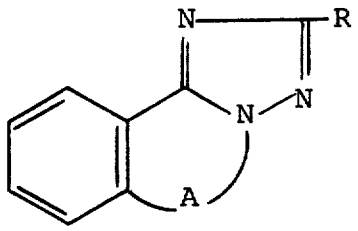

--.

Column 20, Claim 14, formula should read

--

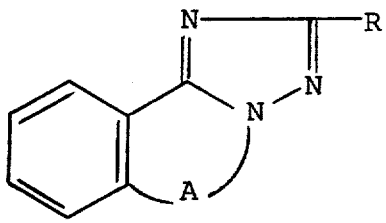

--.

UNITED STATES PATENT AND TRADEMARK OFFICE

CERTIFICATE OF CORRECTION

PATENT NO. : Re. 30,456

DATED : December 23, 1980

INVENTOR(S) : Amedeo Omodei-Sale, et al

It is certified that error appears in the above-identified patent and that said Letters Patent are hereby corrected as shown below:

Column 20, Claim 14, line 46, should read --fluoro, trifluoromethyl, hydroxy, cyclo- --.

Signed and Sealed this

*Twenty-sixth* Day of *May 1981*

[SEAL]

*Attest:*

RENE D. TEGTMEYER

*Attesting Officer* *Acting Commissioner of Patents and Trademarks*